(12) United States Patent
Schultz et al.

(10) Patent No.: US 7,105,152 B1
(45) Date of Patent: Sep. 12, 2006

(54) SUSPENSION AEROSOL FORMULATIONS

(75) Inventors: Robert K. Schultz, San Diego, CA (US); David W. Schultz, St. Paul, MN (US); Robert A. Moris, Lino Lakes, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 08/455,490

(22) Filed: May 31, 1995

Related U.S. Application Data

(60) Division of application No. 07/878,039, filed on May 4, 1992, now abandoned, which is a continuation-in-part of application No. 07/810,401, filed on Dec. 18, 1991, now abandoned, which is a continuation-in-part of application No. 07/809,791, filed on Dec. 18, 1991, now abandoned.

(51) Int. Cl.
*A61K 9/00* (2006.01)
*A01N 25/02* (2006.01)
*A61L 9/04* (2006.01)

(52) U.S. Cl. .......................... 424/43; 424/45
(58) Field of Classification Search ............. 424/43–45
See application file for complete search history.

(56) References Cited

U.S. PATENT DOCUMENTS

| | | | |
|---|---|---|---|
| 2,868,691 A | 1/1959 | Porush et al. ............. 167/54 |
| 2,885,427 A | 5/1959 | Ruh et al. | |
| 3,014,844 A | 12/1961 | Thiel et al. ............... 167/82 |
| 3,219,533 A | 11/1965 | Mullins et al. | |
| 3,261,748 A | 7/1966 | Larsen et al. | |
| 3,320,125 A | 5/1967 | Grim et al. | |
| 3,644,353 A | 2/1972 | Lunts et al. | |
| 3,700,681 A | 10/1972 | Barth | |
| 3,809,294 A | 5/1974 | Torgeson | |
| 3,897,779 A | 8/1975 | Hansen .................. 128/266 |
| 3,994,421 A | 11/1976 | Hansen | |
| 4,044,126 A | 8/1977 | Cook et al. | |
| 4,129,603 A | 12/1978 | Bell | |
| 4,174,295 A | 11/1979 | Bargigia et al. | |
| 4,241,048 A | 12/1980 | Durbak et al. ............. 424/45 |
| 4,311,863 A | 1/1982 | Gumprecht | |
| 4,335,121 A | 6/1982 | Phillipes et al. | |
| 4,347,236 A | 8/1982 | Tanskanen | |
| 4,352,789 A | 10/1982 | Thiel | |
| 4,405,598 A | 9/1983 | Brown | |
| 4,710,495 A | 12/1987 | Bodor | |
| 4,767,612 A | 8/1988 | Hagen et al. | |
| 4,810,488 A | 3/1989 | Jinks | |
| 4,814,161 A | 3/1989 | Jinks et al. ............... 424/45 |
| 4,851,595 A | 7/1989 | Gumprecht | |
| 4,859,696 A * | 8/1989 | Kamiya .................. 514/420 |
| 4,940,171 A | 7/1990 | Gilroy | |
| 4,945,119 A | 7/1990 | Smit et al. | |
| 4,963,557 A | 10/1990 | Badger et al. | |
| 5,118,494 A | 6/1992 | Schultz et al. | |
| 5,126,123 A | 6/1992 | Johnson | |
| 5,145,684 A | 9/1992 | Liversidge et al. | |
| 5,182,040 A | 1/1993 | Bartlett et al. | |
| 5,182,097 A | 1/1993 | Byron et al. ............... 424/45 |
| 5,190,029 A | 3/1993 | Byron et al. ........... 128/200.14 |
| 5,202,110 A | 4/1993 | Dalby et al. | |
| 5,206,268 A | 4/1993 | Latter et al. | |
| 5,225,183 A | 7/1993 | Purewal et al. | |
| 5,230,884 A | 7/1993 | Evans et al. | |
| 5,254,755 A | 10/1993 | Li et al. | |
| 5,270,305 A | 12/1993 | Palmer | |
| 5,290,539 A | 3/1994 | Marecki | |
| 5,292,499 A | 3/1994 | Evans et al. | |
| 5,310,762 A | 5/1994 | Latter et al. | |
| 5,314,682 A | 5/1994 | Sweval et al. | |
| 5,348,730 A | 9/1994 | Greenleaf et al. | |
| 5,427,282 A | 6/1995 | Greenleaf et al. | |
| 5,439,670 A | 8/1995 | Purewal et al. | |
| 5,474,759 A | 12/1995 | Fassberg et al. ............. 424/45 |
| 5,492,688 A | 2/1996 | Byron et al. | |
| 5,508,023 A | 4/1996 | Byron et al. | |
| 5,605,674 A | 2/1997 | Purewal et al. | |
| 5,620,631 A | 4/1997 | Heiskel et al. | |
| 5,653,962 A | 8/1997 | Akehurst et al. | |
| 5,658,549 A | 8/1997 | Akehurst et al. | |
| 5,674,471 A | 10/1997 | Akehurst et al. | |
| 5,674,472 A | 10/1997 | Akehurst et al. | |
| 5,674,473 A | 10/1997 | Purewal et al. | |
| 5,676,929 A | 10/1997 | Akehurst et al. | |
| 5,681,545 A | 10/1997 | Purewal et al. | |
| 5,683,676 A | 11/1997 | Akehurst et al. | |
| 5,683,677 A | 11/1997 | Purewal et al. | |
| 5,688,782 A | 11/1997 | Neale et al. | |
| 5,695,743 A | 12/1997 | Purewal et al. | |
| 5,720,940 A | 2/1998 | Purewal et al. | |
| 5,736,124 A | 4/1998 | Akehurst et al. | |
| 5,744,123 A | 4/1998 | Akehurst et al. | |
| 5,766,573 A | 6/1998 | Purewal et al. | |

(Continued)

FOREIGN PATENT DOCUMENTS

CA    2062854    9/1992

(Continued)

OTHER PUBLICATIONS

*Merck Index*, 12th Edition, 1996.

(Continued)

*Primary Examiner*—Humera N. Sheikh
(74) *Attorney, Agent, or Firm*—Ted Ringsred

(57) ABSTRACT

Pharmaceutical suspension aerosol formulations containing a therapeutically effective amount of a drug and HFC 134a, HFC 227, or a mixture thereof.

14 Claims, No Drawings

U.S. PATENT DOCUMENTS

| | | | |
|---|---|---|---|
| 5,776,432 A | 7/1998 | Schultz | |
| 5,776,433 A | 7/1998 | Tsou et al. | |
| 5,776,434 A | 7/1998 | Purewal et al. | |
| 5,817,293 A | 10/1998 | Akehurst et al. | |
| 5,833,950 A | 11/1998 | Taylor et al. | |
| 5,916,540 A | 6/1999 | Akehurst et al. | |
| 5,919,435 A | 7/1999 | Taylor et al. | |
| 5,922,306 A | 7/1999 | Akehurst et al. | |
| 6,006,745 A | 12/1999 | Marecki | |
| 6,013,245 A | 1/2000 | Taylor et al. | |
| 6,030,682 A | 2/2000 | Marecki | |
| 6,054,488 A | 4/2000 | Oliver et al. | |
| 6,068,832 A | 5/2000 | Berry et al. | |
| 6,200,549 B1 | 3/2001 | Akehurst et al. | |
| 6,221,339 B1 | 4/2001 | Akehurst et al. | |
| 6,238,647 B1 | 5/2001 | Akehurst et al. | |
| 6,251,368 B1 | 6/2001 | Akehurst et al. | |
| 6,303,103 B1 | 10/2001 | Akehurst et al. | |
| 6,306,368 B1 | 10/2001 | Taylor et al. | |
| 6,306,369 B1 | 10/2001 | Akehurst et al. | |
| 6,309,624 B1 | 10/2001 | Sapsford et al. | |
| 6,333,023 B1 | 12/2001 | Akehurst et al. | |
| 6,352,684 B1 | 3/2002 | Purewal et al. | |
| 6,413,497 B1 | 7/2002 | Weil et al. | |
| 6,416,743 B1 | 7/2002 | Fassberg et al. | |
| 6,419,899 B1 | 7/2002 | Weil et al. | |
| 6,503,482 B1 | 1/2003 | Fassberg et al. | |
| 6,743,413 B1 | 6/2004 | Schultz et al. | |
| 6,919,069 B1 | 7/2005 | Akehurst et al. | |
| 2002/0071812 A1 | 6/2002 | Weil et al. | |
| 2004/0013611 A1 | 1/2004 | Schultz et al. | |
| 2004/0197273 A1 | 10/2004 | Schultz et al. | |

FOREIGN PATENT DOCUMENTS

| | | |
|---|---|---|
| CA | 2075058 | 3/2001 |
| DE | 27 03 119 | 8/1977 |
| DE | 2737132 | 2/1978 |
| DE | 30 18 550 | 12/1980 |
| DK | 134923 | 2/1977 |
| EP | 0 039 369 | 11/1981 |
| EP | 0 172 672 | 2/1986 |
| EP | 0 379 793 B1 | 1/1990 |
| EP | 365 119 | 4/1990 |
| EP | 0372777 | 6/1990 |
| EP | 0384371 | 8/1990 |
| EP | 0 403 301 B1 | 12/1990 |
| EP | 0 536 204 | 1/1992 |
| EP | 0 504 112 A2 | 9/1992 |
| EP | 0 518 600 | 12/1992 |
| EP | 0 518 601 | 12/1992 |
| EP | 0 553 298 | 11/1994 |
| EP | 0 656 206 | 6/1995 |
| EP | 0 656 207 | 6/1995 |
| EP | 1 092 430 | 4/2001 |
| GB | 837465 | 6/1960 |
| GB | 1 429 184 | 3/1976 |
| GB | 2 001 334 A | 1/1979 |
| GB | 2 076 422 | 12/1981 |
| GB | 2235627 | 3/1991 |
| GB | 91/26378.0 | 12/1991 |
| GB | 91/26405.1 | 12/1991 |
| GB | 91/26444.0 | 12/1991 |
| GB | 92/02522.0 | 2/1992 |
| JP | 52-80282 | 5/1977 |
| JP | 60-227805 | 11/1985 |
| SE | 437 766 | 3/1985 |
| WO | WO 86/03750 | 7/1986 |
| WO | WO 86/04233 | 7/1986 |
| WO | WO 90/07333 | 7/1990 |
| WO | WO 90/11754 | 10/1990 |
| WO | 91/04011 | 4/1991 |
| WO | 91/11173 | 8/1991 |
| WO | 91/11495 | 8/1991 |
| WO | 91/11496 | 8/1991 |
| WO | 91/14422 | 10/1991 |
| WO | 92/00107 | 1/1992 |
| WO | WO 92/00061 | 1/1992 |
| WO | WO 92/00062 | 1/1992 |
| WO | WO 92/06675 | 4/1992 |
| WO | 92/08446 | 5/1992 |
| WO | WO 92/08447 | 5/1992 |
| WO | WO 92/11190 | 7/1992 |
| WO | 92/22287 | 12/1992 |
| WO | 92/22288 | 12/1992 |
| WO | WO 92/22286 | 12/1992 |
| WO | WO 93/05765 | 4/1993 |
| WO | 93/11743 | 6/1993 |
| WO | 93/11744 | 6/1993 |
| WO | 93/11745 | 6/1993 |
| WO | WO 93/11745 | 6/1993 |
| WO | WO 93/11747 | 6/1993 |
| WO | WO 94/03153 | 2/1994 |
| WO | WO 98/05302 | 2/1998 |
| WO | WO 98/52542 | 11/1998 |

OTHER PUBLICATIONS

Transcript of Judgment by Mr. Justice Pumfrey.
Graepel, P. and Alexander, D.J., *Journal of Aerosol Medicine*, vol. 4, No. 3, 1991.
"CFC-Free Aerosols- The Final Hurdle", *Manufacturing Chemist*, 63(7): 22-23, 1992.
Kontny et al., "Issues Surrounding MDI Formulation Development with Non-CFC Propellants", *Journal of Aerosol Medicine*, 4(3): 181-187, 1991.
Moren, F., "Chlorofluorocarbons (CFCs) and Their Replacement", *The Regulatory Affairs Journal*, Jun. 1991, pp. 385-389.
Dalby, R., "Special Considerations in the Formulatino of Suspension Type Metered Dose Inhalers", *Aerosol Age*, pp. 22-24, 26-28, 34 and 89, Oct. 1990.
Byron, Respiratory Drug Delivery, *CFC Press, Inc.*, Fl., pp. 168-201, 1990.
*Martindale: The Extra Pharmacopoeia*, 28$^{th}$ Edition, Edited by James E.F. Reynolds, Assistant Editor Anne B. Prasad.
The Pharmaceutical Press: London, 1982, Entry No. 1068-t.
Keller, Dr. M., "Alternatives to CFC Containing Dosing Aerosols", Maritim Hotel Cologne, Seminar 538 of the Working Party for Pharmaceutical Process Technology, Mar. 1991.
"Hoechst on the Replacement of CFCs", Sep. 1990, Hoechst Chemikals.
"Hoechst: Development of Alternatives for Fully Halogenated CFC is of Highest Importance", Hoechst Press Information, Oct. 1989.
Byron, 1990, *Respiratory Drug Del.*, CRC Press, Boca Raton, FL, pp. 1-267.
Fassberg et al., 1992, U.S. Appl. No. 07/712,789, filed Jun. 10, 1991.
Fassberg et al., 1992, U.S. Appl. No. 08/157,188, filed as U.S. Appl. No. PCT/US92/04618, filed Jun. 8, 1992.
Fassberg et al., 1993, U.S. Appl. No. 08/157,182, filed Dec. 9, 1993.
1990, "Hoechst to Replace CFCs", Brochure, Heschet um Ersatz von FCKW, Sep. English Translation Provided.
Hammerbeck et al., Inflammation, 24:4:3 17-329, 2000.
Sidhu et al., J. Pharm. Pharmacol., 1993, 45: 597-600.
Morck, H., "EC Commission: CFC Ban in 1997", Pharmazeutische Zeitung, 135(9), pp. 503-503, English translation provided, 1990.
Spauchus, H.O., "HFC 134a as a Substitute Refrigerant for CFC 12", *Rev. Int. Froid*, 11, pp. 389-392, 1988.
"Fluorocarbon/Ozone Alternative to Fully Halogenated Chlorofluorocarbons: The Du Pont Development Program", Du Pont Update, pp. 1-3, 1987.
"ICI Caution of CFC 22", *Chemistry & Industry*, p. 132, Mar. 7, 1988.

"The Quest for 'Ozone Friendly' Gases", *Financial Times*, p. 10, Nov. 11, 1988.

Dolovich, "New Delivery Systems and Propellants", *Can Respir J.*, vol. 6 (3), May/Jun. 1999.

The Merck Index (Budavari, Susan, Editor, Merck & Co., Inc. U.S.A. 1989).

J. A. Ranucci et al., "Controlled Flocculation in Metered'Dose Aerosol Suspensions" *Pharmaceutical Technology*, pp. 69-74, Apr. 1990.

Research Disclosure 16265, Oct. 1997.

Research Disclosure 30161, May 1989.

Oberholz, *Frankfuter Allgemenine Zeitung*, Oct. 1998, vol. 25, No. 207, p. 7.

Dalby et al., *Pharmaceutical Technology*, Mar. 1990, vol. 14, No. 3, pp. 26-33.

*Amzacort carton*, William H. Rorer, Inc., Fort Washington, Pennsylvania, USA 19034, 1986.

*Pharmaceutical Journal*, Sep. 29, 1990, vol. 245, pp. 428-429.

Sciarra, J.J., "Chapter 9: Pharmaceutical Aerosols," *The Theory and Practice of Industrial Pharmacy*, 2$^{nd}$ Ed. 1976 (Philadelphia PA: Lea and Febiger), pp. 270 and 276-278.

Sanders, P.A., Ph.D., *Handbook of Aerosol Technology*, 2$^{nd}$ Edition, 1979 (New York, New York: Van Nostrand Reinhold Company), pp. 30, 32, 33, 166, 167, 232-233, 400-402.

U.S. Senate Hearings, May 12-14, 1987, pp. 343-347,437 (U.S. Government Printing Office, Washington, D.C., 1987), CIS: 1987-S321-26.

*Hagers Handbook of Pharmaceutical Practice*, 1971, pp. 342-354 (Berlin: Springer-Veriag) (with translation).

Gennaro, A.R., *Remington's Pharmaceutical Sciences*, 17th Ed., pp. 1670-1677, 1985.

Pumfrey, J., United Kingdom Patent Court decision, dated Jul. 28, 1998, in the High Court of Justice, Chancery Division, Patent Court, combined cases CH 1997 M No. 3766 and CH 1997 M No. 3722 (re European Patent No. 0 617 610).

Letter to European Patent Office, dated Aug. 10, 1995, in corresponding European Application 93901414.8.

Letter to European Patent Office, dated Nov. 17, 1997, in Opposition to EP 553298.

Expert Report of Dr. John J. Sciarra in U.K. Patents Court, Chancery Division, Revocation Proceedings, CH 1997-M-No. 3722/3766, regarding European Patent 0 617 610.

Expert Report of Ian Smith dated May 27, 1998, U.K. Patents Court, Chancery Division, Revocation Proceedings, CH 1997-M-No.3722/3766, regarding European Patent 0 617 610.

Jacob J., United Kingdom Patents Court decision, dated Jun. 30, 1997, in the High Court of Justice, Chancery Division, Patents Court, combined cases Ch/96/3771 and CH/96/3773 (re European Patent No. 0,372,777, 0,499,344, and 0,553,298).

* cited by examiner

SUSPENSION AEROSOL FORMULATIONS

This is a division of Application Ser. No. 07/878,039 filed May 4, 1992 now abandoned.

This application is a continuation-in-part of commonly assigned, copending applications U.S. Ser. No. 07/809,791 now abandoned and U.S. Ser. No. 07/810,401 now abandoned, both filed Dec. 18, 1991, and both incorporated herein by reference.

BACKGROUND OF THE INVENTION

1. Field of the Invention

This invention relates to pharmaceutical aerosol formulations. In another aspect this invention relates to pharmaceutical suspension aerosol formulations wherein the propellant comprises HFC 134a or HFC 227. In another aspect, it relates to pharmaceutical suspension aerosol formulations containing pirbuterol. In another aspect, it relates to pharmaceutical suspension aerosol formulations containing albuterol sulfate.

2. Description of the Related Art

Pharmaceutical suspension aerosol formulations currently use a mixture of liquid chlorofluorocarbons as the propellant. Fluorotrichloromethane, dichlorodifluoromethane and dichlorotetrafluoroethane are the most commonly used propellants in aerosol formulations for administration by inhalation.

Chlorofluorocarbons (CFCs), however, have been implicated in the destruction of the ozone layer and their production is being phased out. Hydrofluorocarbon 134a (HFC 134a, 1,1,1,2-tetrafluoroethane) and hydrofluorocarbon 227 (HFC 227, 1,1,1,2,3,3,3-heptafluoropropane) are viewed as being more ozone friendly than many chlorofluorocarbon propellants; furthermore, they have low toxicity and vapor pressures suitable for use in aerosols.

Patent Applications WO 91/11495 and WO 91/11496 (both by Weil) describe pharmaceutical suspension aerosol formulations comprising a medicinal agent, optionally a surfactant, and a propellant mixture containing 1,1,1,2,3,3,3-heptafluoropropane and one or more additional components, e.g., pentane, butane, propellant 134a, propellant 11, propellant 125, or propellant 152a.

European Patent Office Publication 0 384 371 (Heiskel) describes solution aerosols in which 1,1,1,2,3,3,3-heptafluoropropane or its mixture with propane, butane, isobutane, dimethyl ether, or 1,1-difluoroethane serves as the propellant. The application does not, however, disclose suspension aerosols or pharmaceutical aerosol formulations.

European Patent Application 89.312270.5 (Purewal et al.) discloses, inter alia, aerosol formulations comprising a medicament, 1,1,1,2-tetrafluoroethane, a surface active agent, and at least one compound having higher polarity than 1,1,1,2-tetrafluoroethane.

U.S. Pat. No. 2,868,691 (Porush et al.) discloses aerosol formulations comprising a medicament, a halogenated lower alkane propellant, and a cosolvent which assists in dissolving the medicament in the propellant. The chemical formula for the propellant given in Col. 2, lines 6–16, generically embraces HFC 134a and HFC 227. Examples of cosolvents disclosed include ethanol and diethyl ether.

U.S. Pat. No. 3,014,844 (Thiel et al.) discloses aerosol formulations comprising a micronized medicament, a halogenated lower alkane propellant and a surface-active agent to assist in the suspension of the medicament in the propellant. The chemical formula for the propellant given in Col. 4, lines 17–28, generically embraces HFC 134a and HFC 227.

Patent Application Wo 90/01454 (Greenleaf et al.) discloses aerosol compositions having HFC 134a as the propellant and comprising a medicament coated with a non-perfluorinated surface active dispersing agent. This application describes control formulations containing only HFC 134a and 0.866 percent by weight of a drug.

Albuterol sulfate is a relatively selective beta-2 adrenergic bronchodilator. It is available in a variety of dosage forms including tablets, syrups and formulations suitable for inhalation. For example, VENTOLIN™ Inhalation Aerosol (commercially available from Allen & Hansburys) is a metered dose aerosol unit containing a microcrystalline suspension of albuterol (free base) in propellant (a mixture of trichloromonofluoromethane and dichlorodifluoromethane) with oleic acid. VENTOLIN ROTOCAPS™ for Inhalation (commercially available from Allen & Hansburys) contain a mixture of microfine albuterol sulfate with lactose and are intended for use with a specially designed device for inhaling powder. VENTOLIN™ Solution for Inhalation (commercially available from Allen & Hansburys) is an aqueous solution of albuterol sulfate intended for use with a nebulizer.

Pirbuterol acetate is a relatively selective beta-2 adrenergic bronchodilator. MAXAIR™ Inhaler (commercially available from 3M Pharmaceuticals, St. Paul, Minn.) is a metered dose aerosol unit containing a fine-particle suspension of pirbuterol acetate in the propellant mixture of trichloromonofluoromethane and dichlorodifluoromethane, with sorbitan trioleate.

SUMMARY OF THE INVENTION

This invention provides a pharmaceutical suspension formulation suitable for aerosol administration, consisting essentially of a therapeutically effective amount of a drug and a propellant selected from the group consisting of HFC 134a, HFC 227, and a mixture thereof, said formulation being further characterized in that it exhibits substantially no growth in particle size or change in crystal morphology of the drug over a prolonged period, is substantially and readily redispersible, and upon redispersion does not flocculate so quickly as to prevent reproducible dosing of the drug.

This invention also provides an aerosol canister containing a formulation as described above in an amount sufficient to provide a plurality of therapeutically effective doses of the drug. Also provided is a method of preparing a formulation as described above, comprising the steps of: (i) combining an amount of the drug sufficient to provide a plurality of therapeutically effective doses and a propellant selected from the group consisting of HFC 134a, HFC 227, and a mixture thereof, in an amount sufficient to propel from an aerosol canister a plurality of therapeutically effective doses of the drug; and (ii) dispersing the drug in the propellant. This invention further provides a method of treating a mammal having a condition capable of treatment by inhalation, comprising the step of administering by inhalation a formulation as described above to the mammal.

In another aspect, this invention provides suspension aerosol formulations comprising a therapeutically effective amount of micronized albuterol sulfate and HFC 227 as substantially the only propellant. This invention also provides suspension aerosol formulations comprising a therapeutically effective amount of micronized albuterol sulfate, from about 0.1 to about 15 percent by weight of ethanol, and HFC 227 as substantially the only propellant. This invention also provides suspension aerosol formulations comprising a therapeutically effective amount of micronized albuterol sulfate, from about 5 to 15 percent by weight of ethanol, from about 0.05 to about 0.5 percent by weight of a surfactant selected from the group consisting of oleic acid and sorbitan trioleate, and HFC 227 as substantially the only propellant.

In another aspect this invention provides suspension aerosol formulations comprising a therapeutically effective amount of micronized pirbuterol acetate and a propellant comprising HFC 227, the formulation being further characterized in that it is substantially free of perfluorinated surfactant. This invention also provides suspension aerosol formulations comprising a therapeutically effective amount of micronized pirbuterol acetate, about 0.1 to about 12 percent by weight of ethanol, and a propellant comprising HFC 227. This invention also provides suspension aerosol formulations comprising a therapeutically effective amount of micronized pirbuterol acetate, about 5 to about 12 percent by weight of ethanol, about 0.05 to about 0.5 percent by weight of oleic acid, and a propellant comprising HFC 227.

This invention also provides a method for inducing bronchodilation in a mammal, comprising administering to the mammal a formulation as described above by inhalation.

DETAILED DESCRIPTION OF THE INVENTION

The term "suspension aerosol formulation" as used herein refers to a formulation in which the drug is in particulate form and is substantially insoluble in the propellant.

Amounts expressed herein in terms of percent refer to percent by weight based on the total weight of the formulation.

The formulations of the invention that consist essentially of drug and a propellant contain drug and propellant in relative amounts such that a formulation suitable for aerosol administration is obtained without the need for additional components. Such formulations preferably contain less than an effective stabilizing amount of surfactant and more preferably are substantially free of surfactant and other components.

The formulations of the invention contain a drug in a therapeutically effective amount, that is, an amount such that the drug can be administered as an aerosol (e.g., topically or by oral or nasal inhalation) and cause its desired therapeutic effect with one dose, or less preferably several doses, from a conventional valve, e.g., a metered dose valve. "Amount" as used herein refers to quantity or to concentration as appropriate to the context. The amount of a drug that constitutes a therapeutically effective amount varies according to factors such as the potency, efficacy, and the like, of the particular drug, on the route of administration of the formulation, and on the device used to administer the formulation. A therapeutically effective amount of a particular drug can be selected by those of ordinary skill in the art with due consideration of such factors. Particularly in formulations of the invention intended for oral inhalation into the lungs, the drug is preferably micronized, i.e., about 90 percent or more of the particles have a diameter of less than about 10 microns, in order to assure that the particles can be inhaled into the lungs.

The particular amount of drug that will remain suspended in a formulation of the invention for a time sufficient to allow reproducible dosing of the drug depends to some extent on the nature of the particular drug, e.g., its density, and on the particular propellant used in the formulation. Generally, however, it has been found that when drug concentrations of less than about 0.1 percent are used in a formulation of the invention the drug flocculates to some degree but generally does not settle or cream to the extent that the suspension becomes unsuitable for use as an aerosol formulation, e.g., in a metered dose inhaler. Therefore as regards drug concentration such formulations are acceptably homogeneous.

When drug concentrations greater than about 0.1 percent but less than about 0.5 percent are used in a formulation of the invention it is sometimes seen that the drug flocculates considerably in the formulation and therefore might have an increased tendency to cream or settle. As discussed below in connection with the propellant component of the formulations of the invention, in these instances it is preferable to select the propellant in a manner that minimizes creaming and settling of the drug in order to assure that the formulation is acceptably homogeneous as regards drug concentration.

As drug concentration increases, e.g., beyond about 0.5 percent, the tendency of the drug to flocculate generally increases also. However, the volume occupied by the flocculated drug also increases and the flocculated drug begins to occupy substantially all of the volume of the formulation. In such instances the flocculated drug often shows a lesser tendency to cream or settle. As regards drug concentration such formulations are acceptably homogeneous.

Generally the concentration of the drug in a formulation of the invention is preferably less than about 0.1 percent, more preferably less than about 0.08 percent, and most preferably less than about 0.05 percent. Accordingly, it is preferred according to this invention that the drug have a potency such that concentrations less than about 0.1 percent, more preferably less than about 0.08 percent, and most preferably less than about 0.05 percent, are therapeutically effective. Preferred drugs for use in the formulations of the invention therefore include formoterol, salmeterol, and pharmaceutically acceptable salts thereof, particularly formoterol fumarate. Other drugs that can be formulated according to this invention include albuterol, beclomethasone dipropionate, cromolyn, pirbuterol, and pharmaceutically acceptable salts and solvates thereof, particularly albuterol sulfate, disodium cromoglycate, and pirbuterol acetate.

The propellant in a formulation of the invention can be HFC 134a, HFC 227, or a mixture thereof in any proportion. The propellant is present in an amount sufficient to propel a plurality of doses from a metered dose inhaler. The density of HFC 134a differs from the density of HFC 227. Therefore the density of the propellant can be adjusted within limits by using mixtures of HFC 134a and HFC 227 in order to accommodate the density of the drug. It is sometimes preferred that the propellant be selected such that the propellant density is as closely matched as possible to the drug density in order to minimize tendencies for the drug to settle or cream, particularly when drug concentration is greater than 0.1 percent or when the drug concentration is between about 0.1 percent and about 0.5 percent.

The pirbuterol acetate formulations of the invention contain a therapeutically effective amount of pirbuterol acetate. Preferably, the pirbuterol acetate constitutes about 0.4 to about 1.0 percent by weight, more preferably about 0.45 to about 0.9 percent by weight, of the aerosol formulation. Preferably the pirbuterol acetate is micronized.

Ethanol can optionally be included in a pirbuterol acetate aerosol formulation of the invention. When ethanol is present it constitutes from about 0.1 to about 12 percent by weight, preferably from about 5 to about 12 percent by weight of the aerosol formulation. In another aspect of this invention ethanol preferably constitutes from about 2 to about 8 percent by weight of the formulation. Oleic acid can optionally be included in a pirbuterol acetate formulation of the invention that includes ethanol. When oleic acid is present it constitutes about 0.01 to about 0.5 percent by weight of the formulation.

Typically the propellant constitutes the remainder of the weight of the formulation once the pirbuterol acetate and the optional ethanol and oleic acid are accounted for. Accordingly the propellant is generally present in an amount of at least about 85 percent by weight based on the total weight of the formulation. The propellant in a pirbuterol acetate formulation of the invention comprises HFC 227, preferably as substantially the only propellant. However, one or more other propellants such as propellant 142b (1-chloro-1,1-difluoroethane), HFC 134a, and the like can be used, preferably in pirbuterol acetate formulations of the invention containing ethanol.

Preferred pirbuterol acetate formulations of the invention exhibit substantially no growth in particle size or change in crystal morphology of the pirbuterol acetate over a prolonged period, are substantially and readily redispersible, and upon redispersion do not flocculate so quickly as to prevent reproducible dosing of pirbuterol acetate.

The albuterol sulfate formulations of the invention contain a therapeutically effective amount of micronized albuterol sulfate. Preferably micronized albuterol sulfate constitutes about 0.2 to about 0.5 percent by weight, more preferably from about 0.35 to about 0.42 percent by weight of the aerosol formulation.

Ethanol can optionally be included in such an albuterol sulfate formulation of the invention. When ethanol is present it constitutes from about 0.1 to about 20 percent by weight, preferably from about 5 to about 15 percent by weight of the formulation. A surfactant selected from the group consisting of oleic acid and sorbitan trioleate can also optionally be included in the formulation when the formulation also includes ethanol. When a surfactant is present it constitutes about 0.01 to about 0.5 percent by weight of the aerosol formulation. Albuterol sulfate formulations of the invention that do not contain ethanol are preferably substantially free of perfluorinated surfactant.

Certain preferred albuterol sulfate suspension aerosol formulations of the invention comprise HFC 227 as substantially the only propellant. Typically the propellant constitutes the remainder of the weight of the formulation once the albuterol sulfate and the optional surfactant and/or ethanol are accounted for. Accordingly the propellant is generally present in an amount of at least about 75 percent by weight based on the total weight of the formulation.

Preferred albuterol sulfate formulations of the invention exhibit substantially no growth in particle size or change in crystal morphology of the albuterol sulfate over a prolonged period, are substantially and readily redispersible, and upon redispersion do not flocculate so quickly as to prevent reproducible dosing of albuterol sulfate.

Generally the formulations of the invention can be prepared by combining (i) the drug in an amount sufficient to provide a plurality of therapeutically effective doses; and (ii) the propellant in an amount sufficient to propel a plurality of doses from an aerosol canister; and dispersing the drug in the propellant. The drug can be dispersed using a conventional mixer or homogenizer, by shaking, or by ultrasonic energy. Bulk formulation can be transferred to smaller individual aerosol vials by using valve to valve transfer methods or by using conventional cold-fill methods.

The pirbuterol acetate suspension aerosol formulations of this invention can be prepared by combining the pirbuterol acetate and the propellant and then dispersing the pirbuterol acetate in the propellant using a conventional mixer or homogenizer. Pirbuterol acetate, however, is somewhat soluble in ethanol alone. Accordingly, when oleic acid and/or ethanol are included in the formulation, it is preferred that the pirbuterol acetate be first placed in an aerosol vial. A mixture of the propellant, oleic acid and/or ethanol can then be added, and the pirbuterol acetate dispersed in the mixture.

The albuterol sulfate suspension aerosol formulations of this invention can be prepared by combining the albuterol sulfate and the propellant and dispersing the albuterol sulfate in the propellant using a conventional mixer or homogenizer. When a surfactant and/or ethanol are included in the formulation, they can be added to the propellant along with the albuterol sulfate.

Aerosol canisters equipped with conventional valves, preferably metered dose valves, can be used to deliver the formulations of the invention. It has been found, however, that selection of appropriate valve assemblies for use with aerosol formulations is dependent upon the particular surfactants or adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC 134a or HFC 227. Moreover, conventional CFC formulations generally contain a surfactant in part as a lubricant for the valve stem. Some formulations of the invention, however, do not contain a surfactant or a lubricant. Therefore certain formulations of the invention are preferably dispensed via a valve assembly wherein the diaphragm is fashioned by extrusion, injection molding or compression molding from a thermoplastic elastomeric material such as FLEXOMER™ DFDA 1137 NT7 polyolefin, FLEXOMER™ DFDA 1138 NT polyolefin, FLEXOMER™ DEFD 8923 NT polyolefin, FLEXOMER™ GERS 1085 NT polyolefin, FLEXOMER™ DFDA 1163 NT7 polyolefin, FLEXOMER™ 1491 NT7 polyolefin, FLEXOMER™ 9020 NT7 polyolefin, FLEXOMER™ 9042 NT polyolefin (Union Carbide), C-FLEX™ thermoplastic elastomer R70-001, C-FLEX™ thermoplastic elastomer R70-051, C-FLEX™ thermoplastic elastomer R70-041, C-FLEX™ thermoplastic elastomer R70-085, C-FLEX™ thermoplastic elastomer R70-003, or C-FLEX™ thermoplastic elastomer R70-026 (Concept Polymer Technologies), or a blend of two or more thereof.

Conventional aerosol canisters, e.g., those of aluminum, glass, stainless steel, or polyethylene terephthalate, can be used to contain a formulation of the invention.

The formulations of the invention can be delivered to the lung by oral inhalation in order to effect bronchodilation or in order to treat a condition susceptible of treatment by inhalation, e.g., asthma, chronic obstructive pulmonary disease. The formulations of the invention can also be delivered by nasal inhalation in order to treat, e.g., allergic rhinitis, rhinitis, or diabetes, or they can be delivered via topical (e.g., buccal) administration in order to treat, e.g., angina or local infection.

The following Examples are provided to illustrate the invention. All parts and percentages are by weight unless otherwise indicated.

EXAMPLE 1

Formulations in HFC 134a

For each of the micronized drug substances A–G set forth below, formulations were prepared at drug concentrations of 0.017 percent, 0.039 percent, 0.083 percent, 0.41 percent, and 1.6 percent by weight based on the total weight of the formulation (corresponding to 0.20 mg/mL, 0.50 mg/mL, 1.0 mg/mL, 5.0 mg/ML, and 20 mg/mL, respectively). The formulations were prepared by dispersing micronized drug in HFC 134a in a sealed 15 mL clear PET vial using ultrasonic energy.

| Drugs: | A | Beclomethasone dipropionate |
|---|---|---|
| | B | Albuterol |
| | C | Albuterol sulfate |
| | D | Formoterol fumarate |
| | E | Disodium cromoglycate |
| | F | Pirbuterol acetate |

For each drug the lowest concentration formulation (0.017 percent by weight) was well dispersed and easily redispersible after standing. None of the formulations at this concentration showed any tendency to flocculate rapidly. As drug concentration increased to 0.41 percent visible flocs started to appear, different drugs having a greater or lesser tendency to flocculate. The increase in flocculation with increasing concentration resulted in an increasing rate of sedimentation or creaming (depending on the particular drug involved) of suspended drug.

As drug concentration was further increased the formulations flocculated but maintained a state of greater homogeneity as the flocculated drug began to occupy more of the formulation volume.

Using time lapse photography 10 and 30 seconds after agitation the formulations were assessed as follows:

| | Drug | | | | | |
|---|---|---|---|---|---|---|
| Concentration (%) | A | B | C | D | E | F |
| 0.017 | + | + | + | + | + | + |
| 0.039 | + | + | + | ? | + | + |
| 0.083 | ? | ? | + | ? | ? | ? |
| 0.41 | − | − | − | − | − | ? |
| 1.63 | + | + | − | + | − | + |

+ = visually acceptable formulation
− = visually unacceptable formulation
? = border line acceptable formulation These results show that each of the drug substances evaluated can be formulated in HFC 134a alone. The formulations retain homogeneity after shaking to form satisfactory formulations for use with a metered dose inhaler. Formulations of low concentration were particularly homogenous. Formulations of intermediate concentration were of varying degrees of acceptability.

At the high concentration of 1.6 percent the drugs with density close to the propellant density (beclomethasone dipropionate and albuterol) formed particularly homogenous suspensions due to the flocculated drug occupying substantially all of the formulation volume. These suspensions would be expected to form satisfactory formulations for use with a metered dose inhaler.

EXAMPLE 2

Formulations in HFC 227

Formulations of disodium cromoglycate (DSCG) were prepared at concentrations of 0.015 percent, 0.035 percent, 0.070 percent, 0.35 percent, and 1.4 percent by weight based on the weight of the formulation with HFC 227 as the propellant in a similar manner to those prepared in Example 1 (again corresponding to 0.20, 0.50, 1.0, 5.0, and 20 mg/mL, respectively).

Formulations were particularly homogenous at concentrations of 0.015 percent, 0.035 percent, and 0.070 percent by weight. At 0.35 percent and 1.4 percent the formulations exhibited more rapid flocculation and sedimentation.

These results show that disodium cromoglycate can be formulated in HFC 227 with no surfactant or other adjuvant.

COMPARATIVE EXAMPLE

Formulations with CFCs

Albuterol sulfate was formulated in two propellant mixes A and B, with no surfactant or adjuvant.

| Propellant mix A: | Propellant 11 | 5% |
|---|---|---|
| | Propellant 114 | 14.25% |
| | Propellant 12 | 80.75% |
| Propellant mix B: | Propellant 11 | 25% |
| | Propellant 114 | 25% |
| | Propellant 12 | 50% |

For each propellant mix the range of drug concentrations used in Example 1 was used.

The formulations at 0.20 mg/mL, 0.50 mg/mL, and 1.0 mg/mL were acceptably homogenous. The formulations at 5.0 mg/mL and 20 mg/mL exhibited relatively rapid flocculation. Notably, all these comparative formulations exhibited more caking of drug on the walls of the container than their HFC 134a counterparts of Example 1.

EXAMPLE 3

Formulation of Formoterol Fumarate with Mixtures of HFC 227 and HFC 134a

Formoterol fumarate was formulated as set forth in Example 1 at concentrations of 0.015 percent, 0.038 percent, 0.076 percent, 0.38 percent, and 1.5 percent (0.20, 0.50, 1.0, 5.0, and 20 mg/mL, respectively) in a 1:1 mixture (W/W) of HFC 134a and HFC 227.

These formulations of formoterol fumarate show reduced flocculation and a slower sedimentation rate than the corresponding formulations of Example 1 above involving HFC 134a alone.

The formulations were photographed using time lapse photography at 10 and 30 seconds post agitation and were assessed as follows:

| Drug Concentration (%) | Assessment |
|---|---|
| 0.015 | + |
| 0.038 | + |
| 0.076 | ? |

-continued

| Drug Concentration (%) | Assessment |
|---|---|
| 0.38 | ? |
| 1.5 | + |

These results show that the use of HFC 227 in combination with HFC 134a as a propellant affords formoterol fumarate suspensions with reduced flocculation and greater homogeneity compared with corresponding formulations with HFC 134a alone as the propellant.

EXAMPLE 4

Formulations of Beclomethasone Dipropionate (BDP)

BDP formulations were prepared at 0.070 percent by weight (1.0 mg/mL) in HFC 227 and at 0.38 percent by weight (5.0 mg/mL) in a 1:1 mixture of HFC 227 and HFC 134a.

The formulation at 0.070 percent in HFC 227 was fairly well dispersed. Flocculation occurred at about 10 seconds after shaking and then creaming about 30 seconds after shaking.

The formulation at 0.38 percent in HFC 134a/HFC 227 involved a drug with a density closely matched to the propellant density. Although flocculation was rapid (small flocs were visible almost immediately after shaking) the flocs neither settled nor creamed.

The results show that it is possible to density match the drug to the propellant mix such that only the flocculation characteristics of the formulations influence homogeneity.

EXAMPLE 5

Salmeterol Formulations in HFC 134a and HFC 227

Formulations of salmeterol free base at 0.02 percent by weight and 0.05 percent by weight were prepared in HFC 134a and in HFC 227 by placing the drug and 5 mL of glass beads into a 15 mL glass vial, crimping on a continuous valve, and adding the appropriate amount of propellant. The formulations were shaken on a paint shaker for 10 min in order to disperse the drug. The drug was seen to cream in both propellants, more so in HFC 227 than in HFC 134a. Flocculation was also apparent. However, the formulations were deemed suitable for use in connection with a metered dose inhaler.

EXAMPLE 6

Formoterol Formulations in HFC 227

A formulation containing 0.01 percent by weight of formoterol fumarate in HFC 227 was prepared in an aerosol canister equipped with a 50 µL SPRAYMISER™ pressure-fill metered dose valve. The formulation was prepared by placing 10 mg formoterol fumarate and 30 mL of glass beads in a 120 mL (4 ounce) glass vial, crimping on continuous valve, and adding 100 g of HFC 227. The vial was then shaken on a paint shaker, chilled, and the contents transferred to 10 mL vials fitted with the metered dose valve. The suspension was acceptably stable to settling and creaming. Valve delivery was measured through the life of the formulations. The results are shown in the Table below.

| | SHOT NUMBER (micrograms per shot) | | | |
|---|---|---|---|---|
| | 1–4 | 54–57 | 107–110 | 160–163 |
| vial #1 | 3.0 | 4.7 | 4.2 | 4.8 |
| vial #2 | 2.7 | 4.1 | 4.1 | 4.1 |
| vial #3 | 4.1 | 5.1 | 4.8 | |
| | 173–177 | | 135–138 | 148–151 |
| vial #1 | 3.1 | | | |
| vial #2 | 3.6 | | | |
| vial #3 | | | 4.8 | 4.0 |

EXAMPLE 7

Formoterol Formulations in HFC 134a

A formulation containing 0.02 percent by weight formoterol fumarate in HFC 134a was prepared and tested using a 50 µL SPRAYMISER™ pressure-fill metered dose valve. Test methods and results are set forth below.

Suspension Aerosol Particle Size Analysis

The particle size distribution of drug in the aerosol suspension is assayed by Malvern Mastersizer™ Particle Size Analyser using a suspending medium of 0.01 percent sorbitan trioleate in heptane.

Using a primed connector, shots are fired via an injection adapter into the Malvern sample cell containing the suspending medium. When a suitable level of obscuration (in the range 8.5–9) is achieved, analysis by laser diffraction is then performed.

The results below show the percentage by weight of particles having particle size below 10.7 µm, below 5.07 µm, and below 1.95 µm. The "Initial" entries represent the average of three independent determinations, and the "25° C.", "CYC", and "HHC" entries represent a single determination after one month under the indicated storage conditions.

| | Unit 1 | | | Unit 2 | | |
|---|---|---|---|---|---|---|
| | Particle Size (µm) | | | | | |
| | <10.7 | <5.07 | <1.95 | <10.7 | <5.07 | <1.95 |
| | Percent by weight | | | | | |
| Initial | 99.6 | 93.4 | 32.2 | 98.0 | 92.6 | 30.5 |
| 25° C. 1 Month | 99.8 | 93.6 | 36.3 | 99.9 | 94.8 | 31.7 |
| CYC 1 Month | 99.8 | 92.9 | 36.1 | 99.8 | 92.5 | 32.5 |
| HHC 1 Month | 99.8 | 93.1 | 33.5 | 99.7 | 92.4 | 34.9 |

25° C.: samples stored at 25° C.
CYC: samples cycled between 15° C. and 37° C., one cycle per day, twelve hours at each temperature
HHC: samples stored in a high humidity cabinet at approximately 40° C. and 85 percent relative humidity This test is carried out at 20° C. using 30 individual canisters. Each canister is primed by firing 10 successive shots just prior to the determination. The weight in mg of one shot from each of the 30 canisters is measured. The average weight of the 30 doses is calculated and recorded as the mean. Also shown below is the number of individual dose weights differing by more than 7.5 percent and by more than 15 percent from the mean weight.

$$\frac{\text{Mean Valve Delivery (mg)}}{59.1} > \frac{7.5\% \text{ from mean}}{0} > \frac{15\% \text{ from mean}}{0}$$

Through Life Delivery

Delivery of drug ex valve is determined by firing ten shots through a stainless steel, circular adapter boss under liquid. The aerosol canister to be examined is primed prior to use. The canister is shaken and allowed to stand for 15 seconds between shots. The sample solutions are assayed by HPLC.

The above test was carried out on shots 6–15, 46–55, and 91–100 of the canister.

|  | Shots | | |
|---|---|---|---|
|  | 6–15 | 46–55 | 91–100 |
|  | Through Life Delivery (µg/dose) | | |
| Initial | | | |
| Unit 1 | 7.19 | 9.18 | 8.77 |
| Unit 2 | 6.55 | 9.20 | 11.77 |
| Unit 3 | 7.17 | 8.99 | 7.53 |
| 1 Month (25° C.) | | | |
| Unit 1 | 9.09 | 9.09 | 8.47 |
| Unit 2 | 8.99 | 9.71 | 7.77 |
| 1 Month (CYC) | | | |
| Unit 1 | 8.58 | 7.86 | 6.82 |
| Unit 2 | 9.12 | 9.29 | 7.75 |
| 1 Month (HHC) | | | |
| Unit 1 | 6.93 | 7.98 | 7.76 |
| Unit 2 | 9.83 | 9.27 | 8.80 |

25° C.: samples stored at 25° C.
CYC: samples cycled between 15° C. and 37° C., one cycle per day, twelve hours at each temperature
HHC: samples stored in a high humidity cabinet at approximately 40° C. and 85 percent relative humidity Twin Stage Impinger Glass impinger apparatus A (BP198 Appendix XV11C) is used. To determine the deposition of the emitted dose, the apparatus is assembled as described. The oral adapter is attached to the throatpiece of the apparatus, and a suitable pump is connected to the outlet of the apparatus. The air flow through the apparatus is 60±5 liters per minute measured at the inlet of the throat. The canister to be examined is primed prior to use, shaken, and allowed to stand for 15 seconds between shots. Ten shots are then fired via the adapter into the apparatus from the canister.

The apparatus is then dismantled and each stage washed with the appropriate amount of methanol. The washings are assayed by HPLC to give the content of the drug found at each stage and also the material balance.

|  | % Stem/Adapter | % Stage 1 | % Stage 2 | Material Balance (%) | Valve Delivery (mg) |
|---|---|---|---|---|---|
| Initial | | | | | |
| Unit 1 | 26.0 | 37.5 | 36.5 | 63.2 | 59.9 |
| Unit 2 | 24.7 | 35.3 | 40.0 | 81.0 | 59.7 |
| Unit 3 | 28.5 | 36.7 | 34.8 | 80.9 | 59.3 |
| 1 Month (25° C.) | | | | | |
| Unit 1 | 52.5 | 23.9 | 23.6 | 80.5 | 58.8 |
| Unit 2 | 52.0 | 16.7 | 31.3 | 76.2 | 52.0 |
| 1 Month (CYC) | | | | | |
| Unit 1 | 16.8 | 53.6 | 29.7 | 70.9 | 57.9 |
| Unit 2 | 24.6 | 47.6 | 27.8 | 82.6 | 60.0 |
| 1 Month (HHC) | | | | | |
| Unit 1 | 33.9 | 37.0 | 29.0 | 82.2 | 59.6 |
| Unit 2 | 15.3 | 60.4 | 24.3 | 81.4 | 60.7 |

25° C.: samples stored at 25° C.
CYC: samples cycled between 15° C. and 37° C., one cycle per day, twelve hours at each temperature
HHC: samples stored in a high humidity cabinet at approximately 40° C. and 85 percent relative humidity

EXAMPLE 8

A 1.35 g portion of micronized pirbuterol acetate, 15.0 g of ethanol and 30 mL of glass beads were placed in a 120 mL (4 ounce) glass aerosol vial. The vial was sealed with a continuous valve, pressure filled with approximately 133 g of HFC 227 and then shaken on a paint shaker for 10 minutes. The resulting formulation contained 0.9 percent by weight of pirbuterol acetate and 10.0 percent by weight of ethanol. The dispersion was transferred into 10 mL aerosol vials which were sealed with 25 µL Spraymiser™ Aerosol Valves (available from Neotechnic Engineering Ltd.).

This formulation was tested for its ability to deliver a consistent dose throughout the "life" of the aerosol by determining the amount of pirbuterol acetate delivered per shot for shots 1, 2, 101, 102, 201, 202, 301 and 302. The amount delivered per shot was determined using the assay described below. The results are shown in the table below.

A firing disk was placed in a 100 mL beaker and submerged in about 30 mL of diluent (55 parts methanol/45 parts 0.1 percent phosphoric acid, v/v). The vial was shaken, inserted into the firing disk, and actuated. The valve and valve stem were rinsed into the beaker with additional diluent. The solution in the beaker was quantitatively transferred to a 100 mL volumetric flask which was then brought to volume with additional diluent. The amount of pirbuterol acetate in the solution was determined using high performance liquid chromatography.

|  | µg Pirbuterol Acetate | | |
|---|---|---|---|
| # of shots | Vial 1 | Vial 2 | Vial 3 |
| 1 | 415.4 | 379.3 | 360.1 |
| 2 | 378.7 | 361.0 | 322.1 |
| 101 | 404.0 | 380.4 | 374.7 |
| 102 | 352.0 | 389.1 | 337.9 |
| 201 | 376.8 | 380.6 | 337.5 |
| 202 | 371.5 | 357.8 | 328.6 |
| 301 | 288.2 | 408.8 | 361.1 |
| 302 | 193.4 | 364.5 | 341.0 |

EXAMPLE 9

A 11.7 g portion of pirbuterol acetate was placed in a beaker then chilled in a dry ice/trichlorofluoromethane bath.

A portion of prechilled HFC 227 was added to the beaker and the resulting slurry was mixed at high speed with a VIRTIS™ Model 45 mixer for at least 3 minutes. The dispersed concentrate was then transferred to a glass bottle and enough prechilled HFC 227 was added to bring the total net content weight to 1300 g. The resulting formulation contained 0.9 percent by weight of pirbuterol acetate. The formulation was transferred to a cold filling system and filled into 10 mL aluminum aerosol vials which were then sealed with 25 μL valves. The formulation was deemed to be suitable for use in connection with a metered dose inhaler.

EXAMPLE 10

A 11.7 g portion of micronized pirbuterol acetate, 3.0 g of oleic acid and 60 g of ethanol were placed in a beaker and homogenized for at least 3 minutes. The resulting slurry was transferred to a tared glass bottle and enough ethanol was added to bring the total weight of the concentrate to 144.7 g. The concentrate was chilled then placed along with 1155 g of prechilled HFC 227 into a prechilled cold filling system. The formulation was filled into 10 mL aluminum aerosol vials which were then sealed with 25 μL Spraymiser™ valves. The resulting formulation contained 0.90 percent by weight of pirbuterol acetate, 0.23 percent by weight of oleic acid and 10.0 percent by weight of ethanol. The formulation was deemed to be suitable for use in connection with a metered dose inhaler.

In Examples 11–12 below, respirable fraction is determined using the test method described below.

Respirable Fraction

In this assay the respirable fraction (the percent by weight of particles having an aerodynamic particle size of less than 4.7 microns) of the aerosol suspension is determined using an Anderson Cascade Impactor (available from Anderson Sampler Inc,; Atlanta, Ga.).

The aerosol vial to be tested is primed five times. The valve and valve stem are then cleaned with methanol and dried with compressed air. The aerosol vial and a clean, dry actuator are coupled to the glass throat attached to the top of the impactor using an appropriate firing adaptor. The calibrated vacuum pump (28.3 L/min) attached to the cascade impactor is turned on. A total of 20 sprays is delivered into the cascade impactor by repeatedly shaking the vial, seating it in the actuator and immediately delivering a single spray. The time between sprays is approximately 30 seconds. The cascade impactor is disassembled and each component is rinsed separately with diluent (55 parts methanol mixed with 45 parts of 0.1 percent aqueous phosphoric acid, v/v). Each solution is analyzed for pirbuterol acetate content using high performance liquid chromatography. The respirable fraction is calculated as follows:

$$\% \text{ respirable} = \frac{\text{drug recovered from plates } 3-7 \times 100}{\text{total drug} - \text{drug recovered from recovered actuator and valve}}$$

EXAMPLE 11

A 1.35 g portion of micronized pirbuterol acetate and 25 mL of glass beads were placed in a 120 mL (4 ounce) glass aerosol vial. The vial was sealed with a continuous valve, pressure filled with approximately 150 g of HFC 227 and then shaken for at least 10 minutes on an automatic shaker. The resulting formulation contained 0.9 percent by weight of pirbuterol acetate. The vial was then charged with 150 psi nitrogen to aid in product transfer to smaller vials. The formulation was transferred to 10 mL aluminum aerosol vials sealed with continuous valves by using a valve to valve transfer button. The vials were then chilled in dry ice then the continuous valves were removed and the vials sealed with 25 μL metering valves. Using the method described above, the respirable fraction was determined in duplicate for two separate vials. Values of 59.1 percent and 54.8 percent were obtained for vial 1. Values of 53.9 percent and 49.3 percent were obtained for vial 2.

EXAMPLE 12

A 1.35 g portion of micronized pirbuterol acetate, 15.0 g of ethanol and 25 mL of glass beads were placed in a 120 mL (4 ounce) glass aerosol vial. The vial was sealed with a continuous valves pressure filled with approximately 134 g of HFC 227 and then shaken on an automatic shaker for at least 10 minutes. The resulting formulation contained 0.9 percent by weight of pirbuterol acetate and 10 percent by weight of ethanol. Individual 10 mL aerosol vials were filled and sealed with 25 μL metering valves using the method described in Example 11. Using the test method described above, the respirable fraction was determined in duplicate for two separate vials. Values of 34.9 percent and 32.5 percent were obtained for vial 1. Values of 31.7 percent and 31.3 percent were obtained for vial 2.

In Examples 13–14 below respirable fraction is determined using the test method described above but using a diluent of 45 parts by volume methanol and 55 parts by volume of 0.1 percent aqueous phosphoric acid.

EXAMPLE 13

A 0.60 g portion of micronized albuterol sulfate and 25 mL of glass beads were placed in a 120 mL (4 ounce) glass aerosol vial. The vial was sealed with a continuous valve and then pressure filled with approximately 150 g of HFC 227 The vial was shaken to disperse the albuterol sulfate. The resulting formulation contained 0.4 percent by weight of albuterol sulfate. The formulation was transferred to 10 mL aluminum aerosol vials sealed with continuous valves by using a valve to valve transfer button. The vials were chilled in dry ice then the continuous valves were removed and the vials were sealed with 25 μL metering valves. Using the method described above, the respirable fraction was determined in duplicate for two separate vials. Values of 69.3 percent and 60.6 percent were obtained for vial 1. Values of 64.0 percent and 63.0 percent were obtained for vial 2.

EXAMPLE 14

A 0.60 g portion of micronized albuterol sulfate, 0.75 g of oleic acid, 22.5 g of ethanol and 25 mL of glass beads were placed in a 120 mL (4 ounce) glass aerosol vial. The vial was sealed with a continuous valve and then pressure filled with approximately 126 g of HFC 227 The vial was shaken to disperse the albuterol sulfate. The resulting formulation contained 0.40 percent by weight of albuterol sulfate, 0.50 percent by weight of oleic acid and 15.0 percent by weight of ethanol. Individual aerosol vials were filled and fitted with 25 μL metering valves using the method described in Example 13. Using the test method described above, the respirable fraction was determined in duplicate for two separate vials. Values of 28.0 percent and 22.0 percent were obtained for vial 1. Values of 27.1 percent and 28.8 percent were obtained for vial 2.

EXAMPLE 15

A suspension aerosol formulation containing 0.37 percent by weight of albuterol sulfate, 0.10 percent by weight of sorbitan trioleate (commercially available under the trade designation Span 85), 9.95 percent by weight of ethanol and 89.58 percent by weight of HFC 227 was prepared. The formulation was deemed to be suitable for use in connection with a metered dose inhaler.

EXAMPLE 16

A 4.5 g portion of ethanol was placed in a 125 mL (4 ounce) glass aerosol vial. The vial was sealed with a continuous valve then pressure filled with 147 g of HFC 227. Portions (approximately 225 mg) of micronized pirbuterol acetate were weighed into 6 separate 15 mL glass aerosol vials. A 5 mL portion of glass beads was added to each vial and the vials were sealed with continuous valves. Each vial was then pressure filled with approximately 19.8 g of the ethanol/HFC 227 solution. The resulting formulation contained 3 percent by weight of ethanol and 0.9 percent by weight of pirbuterol acetate. The vials were then shaken in a paint shaker for 15 minutes. The vials were cooled in dry ice, the continuous valves were removed and the contents poured into separate 15 mL aluminum aerosol vials. The aluminum vials were sealed with 25 µL valves equipped with diaphragms fabricated from C-Flex R-70-051 and tanks seals fabricated from DB218. Using the test method described above, the respirable fraction was determined for two separate vials. Values of 59.8% and 52.8% were obtained. Using the test method described above, the ability of the formulation to deliver a consistent dose throughout the "life" of the aerosol was determined. The results are shown in the table below. The values are the average for the indicated shots.

| | µg Pirbuterol Acetate/shot | |
|---|---|---|
| Shot # | Vial 1 | Vial 2 |
| 1 & 2 | 279.4 | 304.6 |
| 101 & 102 | 197.1 | 329.9 |
| 201 & 202 | 294.9 | 478.1 |
| 301 & 302 | 295.8 | 294.1 |
| 401 & 402 | 269.6 | 350.3 |

EXAMPLE 17

Using the general method of Example 16, 6 vials of a formulation containing 5 percent by weight of ethanol and 0.9 percent by weight of pirbuterol acetate were prepared. Using the method described above, the respirable fraction was determined for two separate vials. Values of 48.2% and 43.5% were obtained. Using the method described above, the ability of the formulation to deliver a consistent dose throughout the "life" of the aerosol was determined. The results are shown in the Table below.

| | µg Pirbuterol Acetate/shot | |
|---|---|---|
| Shot # | Vial 1 | Vial 2 |
| 1 & 2 | 263.9 | 288.5 |
| 101 & 102 | 283.5 | 325.4 |
| 201 & 202 | 300.6 | 367.2 |
| 301 & 302 | 330.7 | 306.6 |
| 401 & 402 | 312.8 | 270.5 |

What is claimed is:

1. A pharmaceutical suspension aerosol formulation consisting essentially of:
   (i) particulate drug;
   (ii) 1,1,1,2-tetrafluoroethane as propellant; and
   (iii) ethanol in an amount of 5 to about 15 percent by weight, wherein the formulation is further characterized in that it contains no surfactant.

2. The pharmaceutical suspension aerosol formulation of claim 1, wherein the drug is micronized.

3. An aerosol canister equipped with a metering valve, containing a formulation according to claim 1 in an amount sufficient to provide a plurality of therapeutically effective doses of the drug.

4. The pharmaceutical suspension aerosol formulation of claim 1, wherein the particulate drug is selected from the group consisting of formoterol, salmeterol, beclomethasone dipropionate, cromolyn, pirbuterol, albuterol, and pharmaceutically acceptable salts or solvates thereof.

5. The pharmaceutical suspension aerosol formulation of claim 4, wherein the particulate drug is formoterol or a pharmaceutically acceptable salt or solvate thereof.

6. The pharmaceutical suspension aerosol formulation of claim 5, wherein the particulate drug is formoterol fumarate.

7. The pharmaceutical suspension aerosol formulation of claim 4, wherein the particulate drug is salmeterol or a pharmaceutically acceptable salt or solvate thereof.

8. The pharmaceutical suspension aerosol formulation of claim 4, wherein the particulate drug is albuterol or a pharmaceutically acceptable salt or solvate thereof.

9. The pharmaceutical suspension aerosol formulation of claim 8, wherein the particulate drug is albuterol sulfate.

10. The pharmaceutical suspension aerosol formulation of claim 4, wherein the particulate drug is pirbuterol or a pharmaceutically acceptable salt or solvate thereof.

11. The pharmaceutical suspension aerosol formulation of claim 10, wherein the particulate drug is pirbuterol acetate, and the range of ethanol is from 5 to 12 percent by weight.

12. The pharmaceutical suspension aerosol formulation of claim 4, wherein the particulate drug is beclomethasone dipropionate a pharmaceutically acceptable solvate thereof.

13. The pharmaceutical suspension aerosol formulation of claim 4, wherein the particulate drug is cromolyn or a pharmaceutically acceptable salt or solvate thereof.

14. The pharmaceutical suspension aerosol formulation of claim 13, wherein the particulate drug is disodium cromoglycate.

* * * * *

UNITED STATES PATENT AND TRADEMARK OFFICE
CERTIFICATE OF CORRECTION

PATENT NO. : 7,105,152 B1
APPLICATION NO. : 08/455490
DATED : September 12, 2006
INVENTOR(S) : Robert K. Schultz It is certified that error appears in the above-identified patent and that said Letters Patent is hereby corrected as shown below:

First Page Col. 1 (U.S. Patent Documents):
Line 26, After "Kamiya" insert -- et al. --.

Page 2, Col. 2 (Other Publications):
Line 11, Delete "Formulatino" and insert -- Formulation --, therefor.
Line 23, Delete "Chemikals." and insert -- Chemicals. --, therefor.
Line 34, Delete "Sep." and insert -- Sep., --, therefor.
Line 35, Delete "3 17-329" and insert -- 317-329 --, therefor.
Line 38, Delete "pp. 503–503," and insert -- p. 503, --, therefor.

Page 3, Col. 1 (Other Publications):
Line 10, Delete "Oct." and insert -- Oct., --, therefor.
Line 11, Delete "May" and insert -- May, --, therefor.

Page 4 Col. 2 (Other Publications):
Line 10, Delete "93901414.8." and insert -- 93/901414.8. --, therefor.
Line 19, After "Jacob" insert -- , --.

Column 2:
Line 4, Delete "Wo" and insert -- WO --, therefor.

Column 7:
Line 10, Delete "ML," and insert -- mL, --, therefor.

Column 10:
Line 61, Above "This test" insert -- VALVE DELIVERY --.

Column 13:
Line 38, Delete "Inc,;" and insert -- Inc., --, therefor.

UNITED STATES PATENT AND TRADEMARK OFFICE
CERTIFICATE OF CORRECTION

PATENT NO. : 7,105,152 B1
APPLICATION NO. : 08/455490
DATED : September 12, 2006
INVENTOR(S) : Robert K. Schultz It is certified that error appears in the above-identified patent and that said Letters Patent is hereby corrected as shown below:

Column 14:
Line 21, Delete "valves" and insert -- valve, --, therefor.

Signed and Sealed this

Thirtieth Day of January, 2007

JON W. DUDAS
*Director of the United States Patent and Trademark Office*